United States Patent
Dosmann et al.

(10) Patent No.: US 7,304,743 B2
(45) Date of Patent: Dec. 4, 2007

(54) DIFFUSE REFLECTANCE READHEAD

(75) Inventors: Andrew J. Dosmann, Granger, IN (US); Mohammad A. Kheiri, Elkhart, IN (US)

(73) Assignee: Bayer Healthcare, LLC, Tarrytown, NY (US)

( * ) Notice: Subject to any disclaimer, the term of this patent is extended or adjusted under 35 U.S.C. 154(b) by 447 days.

(21) Appl. No.: 10/739,227

(22) Filed: Oct. 27, 2003

(65) Prior Publication Data

US 2004/0090615 A1     May 13, 2004

Related U.S. Application Data

(60) Provisional application No. 60/421,626, filed on Oct. 29, 2002.

(51) Int. Cl.
*G01N 21/47*     (2006.01)
*G01N 21/55*     (2006.01)

(52) U.S. Cl. ........................... 356/446; 356/445

(58) Field of Classification Search ......... 356/445–446
See application file for complete search history.

(56) References Cited

U.S. PATENT DOCUMENTS

| | | | |
|---|---|---|---|
| 3,910,701 A * | 10/1975 | Henderson et al. ............ 356/39 |
| 4,265,545 A * | 5/1981 | Slaker ......................... 356/431 |
| 4,603,976 A * | 8/1986 | Fetzer et al. ................. 356/402 |
| 4,838,697 A * | 6/1989 | Kurandt ....................... 356/406 |
| 5,090,795 A * | 2/1992 | O'Meara et al. ............. 359/240 |
| 5,278,816 A * | 1/1994 | Russell ................... 369/109.02 |
| 5,518,689 A | 5/1996 | Dosmann et al. ......... 422/82.05 |
| 5,611,999 A | 3/1997 | Dosmann et al. ......... 422/82.05 |
| 5,723,282 A | 3/1998 | Fahy et al. ................... 435/1.3 |
| 5,790,259 A * | 8/1998 | Mizuhata et al. ............ 356/445 |
| 5,866,349 A | 2/1999 | Lilja et al. |
| 6,043,506 A * | 3/2000 | Heffelfinger et al. ........ 250/584 |
| 6,152,942 A | 11/2000 | Brenneman et al. ......... 606/181 |
| 6,181,417 B1 | 1/2001 | Dosmann ..................... 356/326 |

FOREIGN PATENT DOCUMENTS

WO     WO01/43113     6/2001

\* cited by examiner

*Primary Examiner*—Tarifur Chowdhury
*Assistant Examiner*—Isiaka Akanbi
(74) *Attorney, Agent, or Firm*—Nixon Peabody LLP

(57) ABSTRACT

A glucose monitoring system comprising a readhead positioned a predetermined distance from a sample aperture. The readhead comprises first and second LEDs adapted to emit intersecting paths of light. A beam splitter is positioned at the intersection of the light paths. The beam splitter comprises a band pass filter for controlling the center wavelength of a resulting coaxial emitted light for illuminating a sample on the sample aperture. The readhead further comprises a detector which comprises a detector aperture and a molded lens over the detector aperture. A light-scattering section upstream of the lens comprises a plurality of steps having angles greater than 90 degrees to reduce internal stray light.

31 Claims, 4 Drawing Sheets

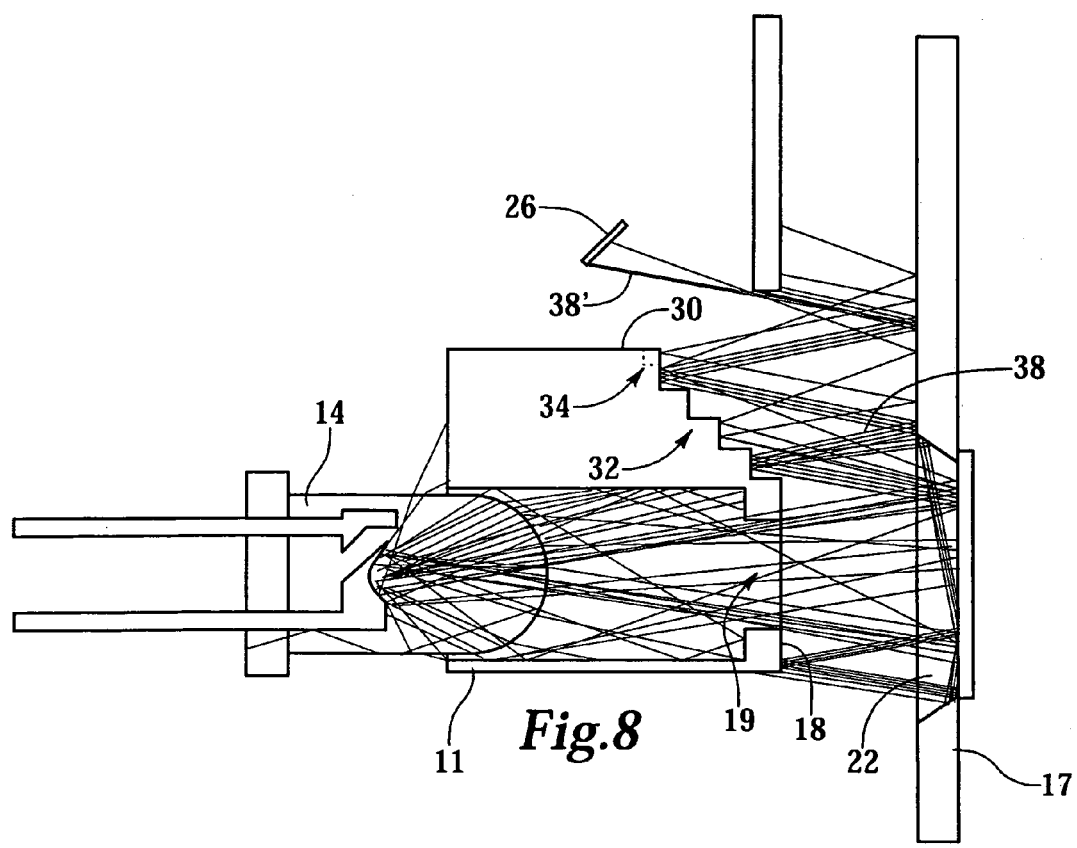
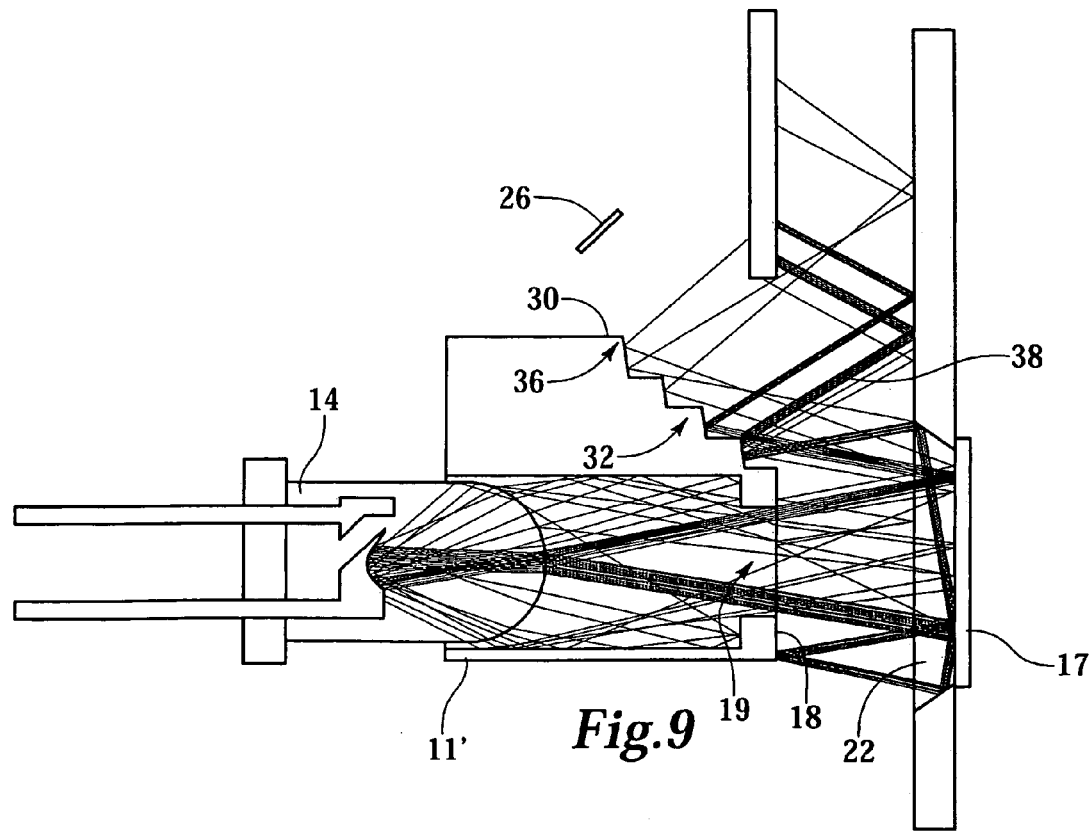

DIFFUSE REFLECTANCE READHEAD

CROSS-REFERENCE TO RELATED APPLICATION

This application claims the benefit of the U.S. Provisional Application 60/421,626, filed on Oct. 29, 2002, which is hereby incorporated by reference in its entirety.

FIELD OF THE INVENTION

The present invention relates generally to blood monitoring devices with some embodiments related to glucose monitoring systems. Particular embodiments relate to a diffuse reflectance device for use with a glucose monitoring system.

BACKGROUND OF THE INVENTION

It is often necessary to quickly obtain a sample of blood and perform an analysis of the blood sample. One example in which there is a need for obtaining a sample of blood is in connection with a blood glucose monitoring system where a user must frequently use the system to monitor the user's blood glucose level.

Those who have irregular blood glucose concentration levels are medically required to regularly self-monitor their blood glucose concentration level. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky and confused. That person's judgment may become impaired and that person may eventually pass out. A person can also become very ill if his blood glucose level becomes too high—a condition known as hyperglycemia. Both conditions, hypoglycemia and hyperglycemia, are potentially life-threatening emergencies. Therefore obtaining accurate test results is highly important.

One method of monitoring a person's blood glucose level is by portable hand-held blood glucose testing devices. The portable nature of these devices enables the user to conveniently test his blood glucose level wherever the user may be. To check the blood glucose level a drop of blood is obtained from him, for example from the fingertip, using a separate lancing device. Once the requisite amount of blood is produced on the fingertip, the blood is harvested using the blood glucose-testing device. The blood is drawn inside the testing device, which then determined the concentration of glucose in the blood. The results of the test are communicated to the user by a display on the testing device. More detail concerning lancing devices is set forth in U.S. Pat. No. 6,152,942, which is commonly assigned and incorporated herein by reference in its entirety.

Drawbacks associated with optical instruments for reading calorimetric reactions include size, low signal throughput and accuracy errors which are due, in part, to mechanical alignment (or mis-alignment) sensitivity of the optical components. These problems are further compounded when the optical instruments require readings at more than one wavelength or at multiple wavelengths. Providing multiple wavelengths compound these problems because prior art devices produce light of each wavelength with a different light element such as a light emitting diode. Each of the light emitting diodes can not be linearly aligned, or identically aligned, with the sample. This results in the light from each of the light emitting diodes having a different intensity and different intensity distribution across the sample.

Many glucose-monitoring systems determine a concentration of glucose in the blood sample by measuring the diffused reflectance from a reagent. The reagent has a color change that is proportional to the concentration of glucose in the blood sample. Generally, diffused reflectance is the preferred method of reading the change in color of the reagent. Additional background concerning colorimetric testing and diffuse light reflectance is found in U.S. Pat. Nos. 5,723,284; 6,181,417B1; 5,518,689; 5,611,999, all of which are incorporated herein by reference in their entirety.

Current methods of reading diffuse reflectance use LEDs as a monochromatic source of illumination. The problem with using an LED is that a typical center wavelength tolerance of plus or minus 20 nm causes a variation in the diffused reflectance. The variation in wavelength around the center wavelength will cause the reagent color to vary around a reflectance corresponding to the center wavelength of the LED. This reflectance variation translates into an error in glucose concentration. An error in glucose concentration level can lead the user to take too much medicine or avoid taking enough medicine, thereby resulting in a potential seizure, coma, or even death. Thus obtaining accurate glucose concentration levels in a blood sample is critical.

One category of diffuse reflectance is two-wavelength diffuse reflectance. Current designs of two-wavelength diffuse reflectance readheads use coaxial sample illumination from LEDs at two different wavelengths. The coaxial illumination of the sample by the two LEDs is traditionally done with a beam splitter. Another method is to illuminate the sample with both LEDs tilted 15 degrees off the sample's normal optical axis.

One method for reducing the reflectance variation due to tolerance of the LED is to sort the LEDs according to tight center wavelength tolerances to reduce the spectral errors. Such sorting processes can increase the cost of LEDs by up to 15 times their nominal cost. A low cost alternative to reducing the spectral errors caused by LED center wavelength variation is taught herein. A method of coaxially illuminating the sample to be analyzed is also taught herein. Additional advantages concerning illumination, detection and blood monitoring, generally, will be apparent to those of ordinary skill in the art from the teachings herein.

OBJECT OF THE INVENTION

An object of the invention is to provide an improved blood monitoring system. A further object is to reduce cost of components associated with a blood monitoring device and in particular a glucose monitoring device.

An object of the invention is to provide improved accuracy and precision associated with results of monitoring systems. A further object is to provide improved results with use of coaxial illumination via two wavelengths.

Another object is to provide an improved method of controlling variation of center wavelengths of illumination.

Another object is to provide diffuse reflectance analysis using relatively narrow bandwidth illumination from typical off the shelf off-the-shelf LEDs having a typical center wavelength tolerance, where the narrow bandwidth is less than the variance of the LEDs. A further object is to control center wavelength with a LED, filter and beam splitter combination.

Another object is to provide an improvement for reducing internal stray light entering a detector active area in a diffuse reflectance detector.

Another object is to provide an improved monochromatic source of illumination.

Another object is to provide more accurate results for analysis based on light illumination and other techniques.

Another object is to provide an improved readhead for use in a diffuse reflectance system.

Other objects and advantages will be apparent to those of ordinary skill in the art from the teachings herein.

SUMMARY OF THE INVENTION

An embodiment of the invention is directed toward an illumination source. One such embodiment comprises a first monochromatic illumination source which comprises an associated illumination center-wavelength and associated illumination tolerance. A source emits rays defining an illumination path. A bandpass filter is positioned in the illumination path. The filter comprises an associated filter center-wavelength and an associated filter tolerance. For some applications, the filter tolerance is selected to be approximately equal to one-half the illumination tolerance with the filter center-wavelength selected to be approximately equal to the illumination center-wavelength minus the illumination tolerance.

A related embodiment of the invention is directed toward a readhead. One such embodiment comprises a first LED having a first center-wavelength associated therewith wherein the LED is adapted to emit a first path of light. A second LED comprising a second center-wavelength is adapted to emit a second path of light that intersects the first path of light at an intersection. The readhead further comprises a beam splitter positioned at the intersection wherein the beam splitter comprises a bandpass filter. The first LED, the second LED and the beam splitter are arranged to provide coaxial illumination in a first direction. For some applications, the bandpass filter comprises a relatively narrow bandpass as compared to a bandwidth or spectra associated with the first LED. At least a portion of the coaxial illumination is reflected off of a sample, thereby creating diffuse reflective light. The readhead further comprises a detector located to receive at least a portion of the diffused reflected light.

In some embodiments, the readhead is adapted for use in a monitoring system which is adapted to receive a sample and determine a parameter value, such as a glucose concentration level, based on analyzing the sample. In such an embodiment, a readhead may comprise a first LED having a first-wavelength and a first tolerance associated therewith. The first LED is adapted to emit a first path of light. A beam splitter comprising a bandpass filter is positioned in the first path of light. The beam splitter comprises a filter center-wavelength and a filter tolerance. A second LED is fixedly positioned relative to the first LED and the beam splitter. The second LED comprises a second center-wavelength and a second tolerance associated therewith. The second LED is adapted to emit a second path of light that intersects the beam splitter. The second LED, the beam splitter and the first LED are positioned to provide co-axial illumination of the sample by the first and second LEDs.

For some applications, the filter tolerance is selected to be less than the first tolerance associated with the first LED. The bandpass filter selected comprises a relatively narrow bandpass as compared to a bandwidth associated with the first LED.

The readhead further comprises a face defining an exit aperture through which the coaxial illumination passes. A sample aperture is spaced a predetermined distance from the face and positioned to be illuminated by the coaxial illumination. Thus, when a sample is located on the sample aperture, the sample will reflect the co-axial illumination.

A detector is positioned to receive at least a portion of the diffuse reflected coaxial illumination through a detection aperture. In some applications a lens is placed over the detection aperture to focus light onto an active area of the detector. The lens preferably comprises a plurality of steps defining one or more angles greater than 90 degrees. The steps of the lens are angled to reduce stray non-diffuse light rays reflected off the sample from reaching the detection area.

BRIEF DESCRIPTION OF THE DRAWINGS

FIG. 8 shows light rays reflected from a conventional molded readhead housing having 90 degree steps.

FIG. 9 shows light rays reflected from a modified molded readhead housing having 100 degree steps.

DESCRIPTION OF ILLUSTRATIVE EMBODIMENTS

Figure 1:
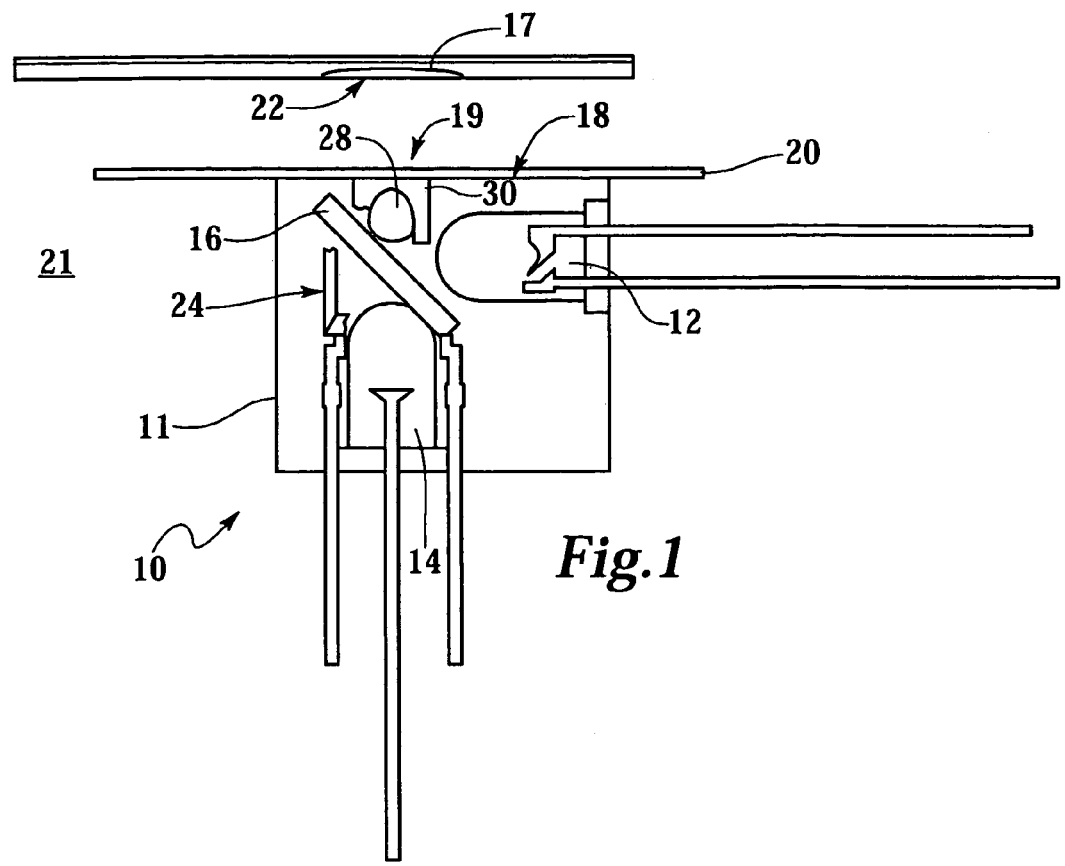
FIG. 1 shows a top view of a readhead spaced from a sample aperture.
Figure 2:
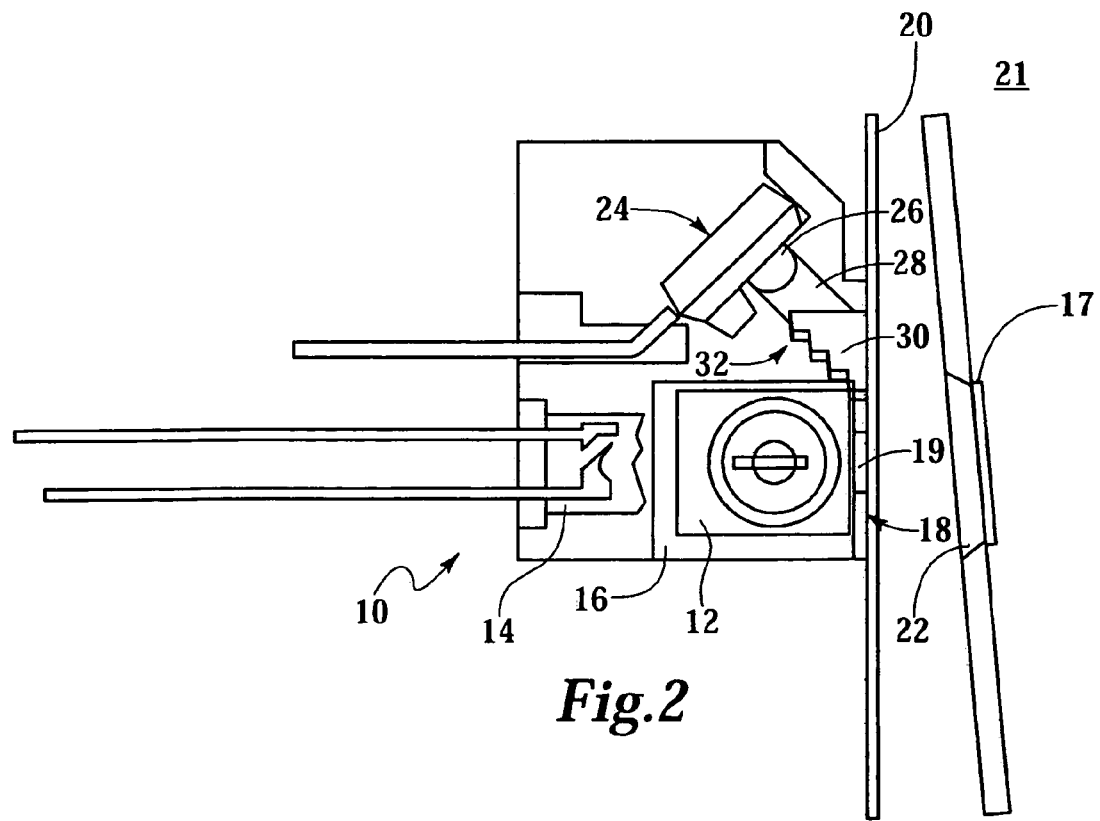
FIG. 2 shows a side view of the readhead and sample aperture shown in FIG. 1

FIGS. 1 and 2 show top and side views of a readhead 10, respectively. In particular the illustrated readhead is a 2-wavelength diffused-reflectance readhead. FIG. 1 illustrates a housing 11 supporting a first horizontal LED 12 which has a center wavelength of 940 nm. A second vertical LED 14 having a center wavelength of 700 nm is supported in the housing 11 at right angles to the first LED 12. In FIG. 2, part of the second LED 14 is cut away for clarity. One of ordinary skill in the art will understand that teachings disclosed herein are not limited to specific wavelength or sizes of LEDs. A dichroic beam splitter 16 is arranged relative to the first LED 12 and the second LED 14 to provide coaxial illumination of a sample 17 by both LEDs.

A face 18 defines an exit aperture 19 through which the coaxial illumination passes. A 0.20 mm thick polycarbonic window 20 is located over the face 18 of the readhead 10 to prevent readhead contamination.

A monitoring system 21 comprises a sample aperture 22 tilted 5 degrees off of the normal to prevent specular sample reflections from reaching a detector 24. In FIG. 1, part of the detector 24 is cut-away to better show the beam splitter 16. In a preferred embodiment, a 4.57 mm diameter sample 17 is located over a 3.81 mm by 4.32 mm oval sample aperture 22. The sample 17 is located 3.175 mm away from the readhead 10. The exit aperture is sized to produce a 3.300 mm diameter beam at the sample.

The detector 24, in a preferred embodiment, is a TAOS LS250 monolithic detector/amplifier, which is located perpendicular to the 45 degree reflection axis. The detector 24 comprises an active area (not shown) approximately 1.50 mm squared. A portion of the diffused reflective light passes through a detection aperture 28, which is also 1.5 mm squared and is positioned at the 45 degree angle. A conventional TAOS package includes a molded lens 26 downstream of the detector aperture 28 to focus incoming light onto the active area of the detector 24. Typically the readhead housing comprises a light-scattering section 30 upstream of the detection aperture 28. The light-scattering section comprises a plurality of steps 32 formed at rear right angles.

Figure 3:
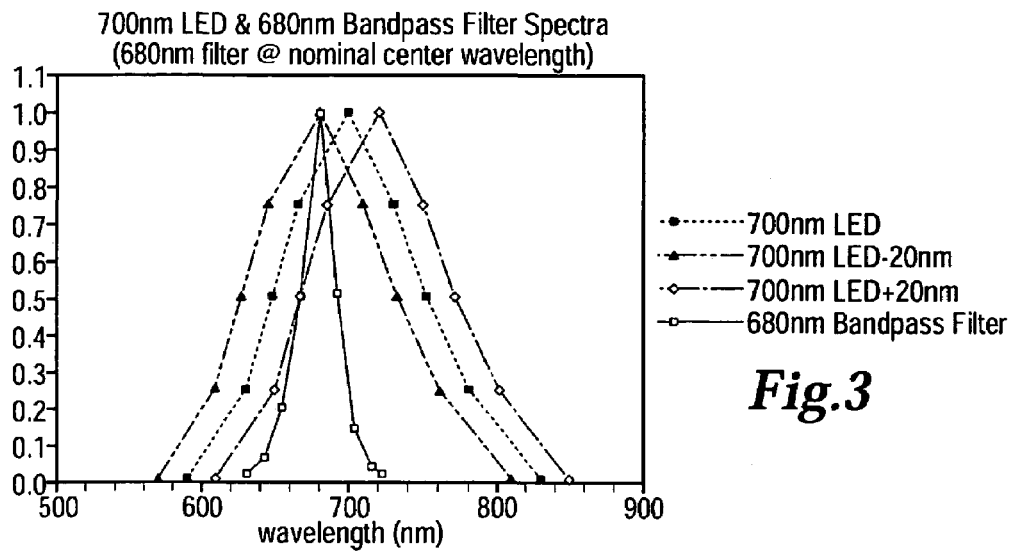
FIGS. 3-5 graphically illustrate 700 nm LED and 680 nm bandpass filter spectra.
Figure 4:
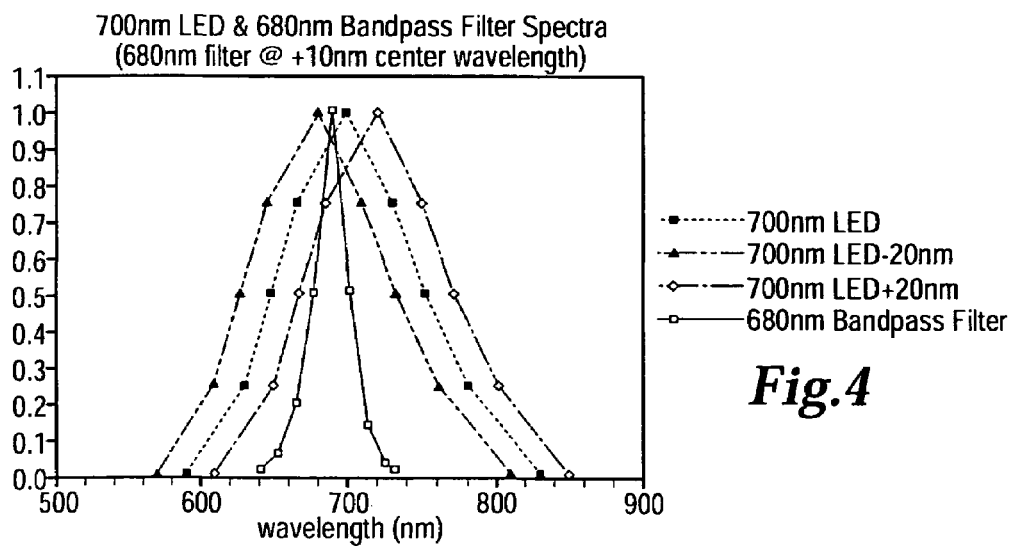
Figure 5:
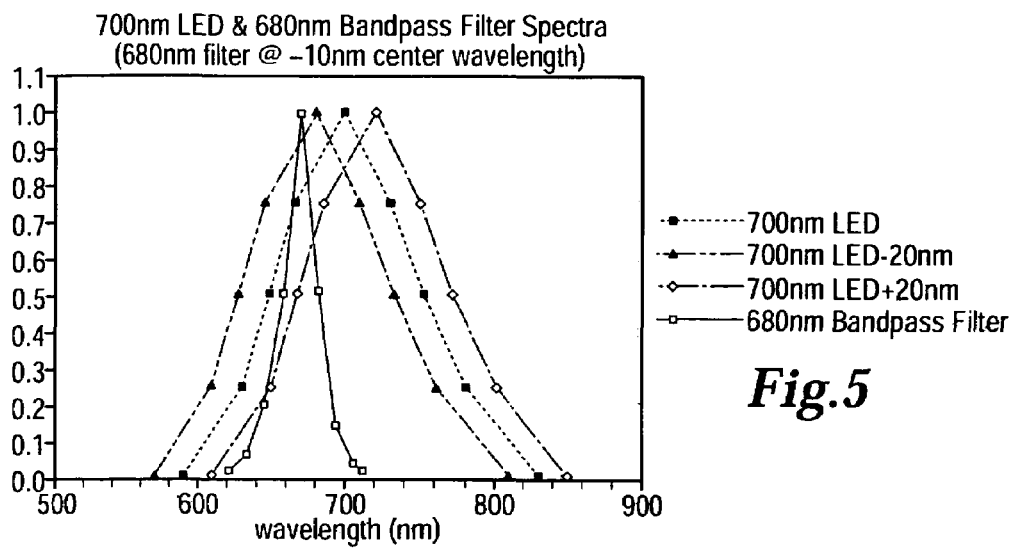

FIGS. 3, 4 and 5 depict the spectrum of the first LED comprising a 700 nm center-wavelength with a 20 nm tolerance. The first LED has a bandwidth of approximately 100 nm. Assume the same typical characteristics for the second LED, except that the center wavelength of the second LED is positioned at 940 nm. One of ordinary skill in the art will observe that the upper spectra of the first LED falls at 820 nm and the lower spectra of the second LED also falls at 820 nm. Thus even with a separation of 240 nm between center wavelengths, there is a potential overlap in the beam comprising co-axial illumination formed from the first LED and the second LED.

To prevent overlap between the rays from the first LED and the second LED, a bandpass filter is used with the beam splitter. In a preferred embodiment, the bandpass filter is a two color filter integral with the beam splitter. The beam splitter is thereby preferably a dichroic beam splitter 16. Other beam splitter and bandpass filter combinations, in accordance with the teachings herein, will be apparent to those of ordinary skill in the art.

FIGS. 3-5 illustrate use of a 25 nm full width half-maximum bandpass filter for the beam splitter 16. The filter center wavelength is set at 680 nm. The filter tolerance used in FIGS. 3-5 is 10 nm. The center wavelength tolerance of 10 nm is commonly available at a low cost. Examining FIGS. 3-5 at the full width half maximum (FWHM) it is apparent that, with reference to FIG. 3, there are only minor variations in center wavelength characteristics of the filtered 700 nm LED light with a plus or minus 20 nm LED center wavelength shift. similarly, FIGS. 4 and 5 show a plus or minus 20 nm variation in center wavelength of the LED spectra with the bandpass filter center wavelength of 680 nm plus or minus 10 nm.

The only condition that significantly alters the filtered center wavelength is when the LED center wavelength is at 700 nm plus 20 nm and the filter center wavelength is at 680 nm minus 10 nm. This condition forces the combined center wavelength toward a nominal 680 nm. Therefore, large center wavelength variations plus or minus 20 nm will not significantly change the spectra output of the splitter 16.

Figure 6:
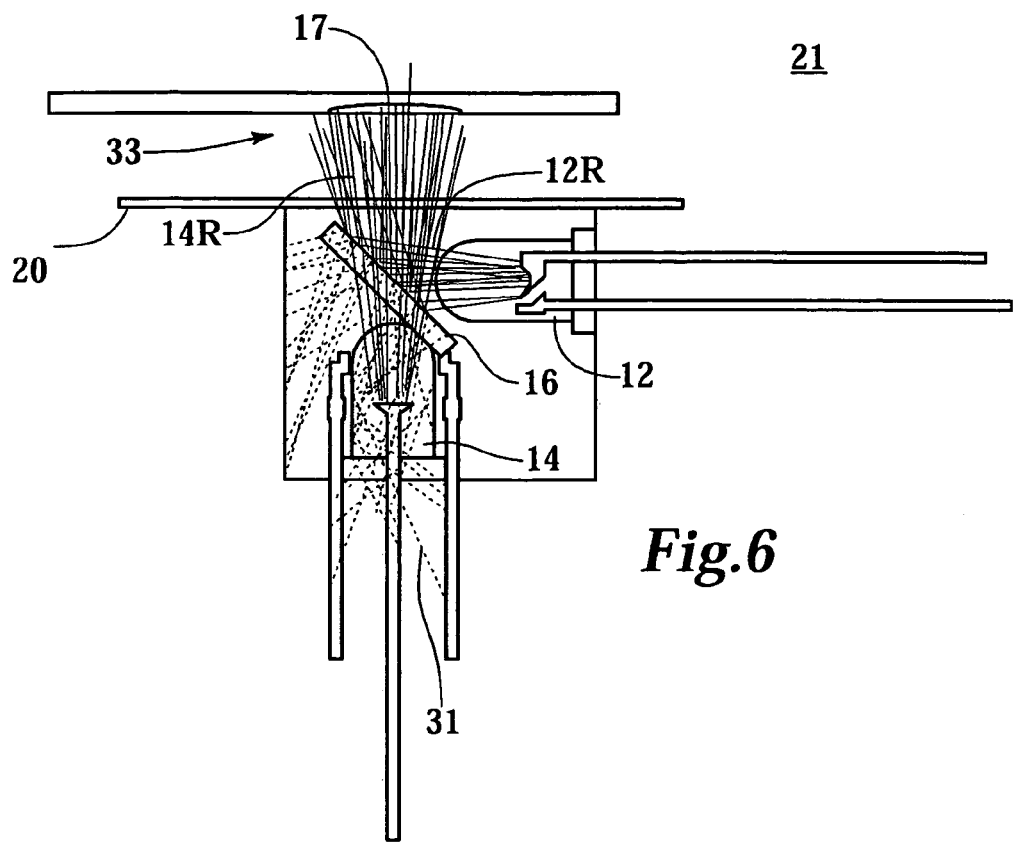
FIG. 6 shows a top view of a 700 nm LED illuminating a dichroic filter.

FIG. 6 illustrates out-of-band rays 31 blocked by the splitter 16 while in-band rays 14R are passed through the splitter 16. All of the 940 nm rays 12R associated with the second LED reflect off the bandpass filter 16 to illuminate the sample aperture 22, and thereby the sample. The two sets of rays 14R and 12R combine to illuminate the sample aperture 22. Detector 24 is removed for clarity.

Use of a combination beam splitter and bandpass filter, such as a dichroic filter, results in a significant cost savings. For example, the difference in cost between a custom 680 nm T1 LED with a specific bend width (Shinkoh Electronics Corporation, QDI KL724-680) and a 700 nm T1 LED (Lite-On Inc., LTL-4212) is approximately $4.00. A cost estimate of the dichoric filter (beam splitter) is a $1.09 (OCLI Inc.) a cost savings of approximately $3.00 could be realized with a 700 nm LED in a band pass filter combination. The cost of the TAOS detector is $1.02 (at 50 k/year). The new readhead design provides a two wavelength diffuse reflectance readhead at a low cost. Thus current components cost approximately $11.00 while the readhead according to the teachings hearing cost approximately $3.00 to $4.00

Figure 7:
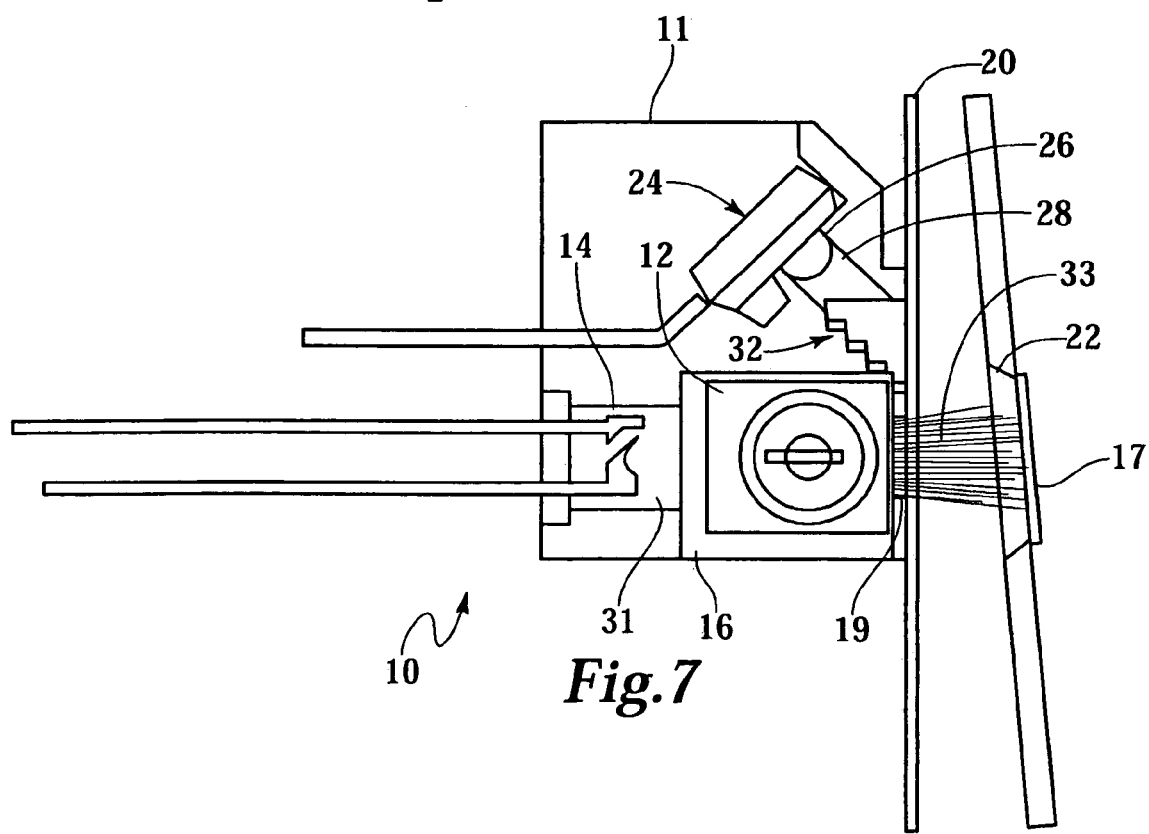
FIG. 7 shows a detector aligned with the 45 degree reflectance angle.

FIGS. 6 and 7 show the 700 nm T1 LED illuminating the dichoric 680 nm bandpass filter 16. The detector 24 is mounted at a 45 degree angle from the sample normal axis to detect a diffuse reflected light. Spectra reflections of the sample are directed away from the detector 24 active area or blocked from reaching the detector active area by steps 32 within the light-scattering section 30.

The filter 16 passes a 25 nm bandwidth of light at a center wavelength of 680 nm plus and minus 5 nm, i.e., 650 nm to 710 nm. A filtered light passes through a two millimeter diameter exit aperture 19. And the 940 nm T1 LED output reflects off of the dichroic beam splitter 16 and passes through the two millimeter diameter exit aperture 19. Together, LEDs 12 and 14 illuminate the sample with a 3.3 millimeter diameter coaxial beam 33.

Two readhead housings (11, 11'), depicted in FIGS. 8 and 9, were modeled with light-scattering steps 32 at 90 a degree angle (ref. no. 34) and at a 100 degree angle (ref. no. 36). For simplicity, as well as to minimize test variables, one LED 14 was used; a filter and a second LED were not incorporated into the angle-step test. The steps are designed to prevent specular reflections off of the sample from reaching the detector active area 26, which reduces internal stray light (i.e., non-diffused light). The 90 degree step 34 is more likely to reflect a specular ray 38 back-up into the sample aperture 22, where the ray 38' can reflect back onto the detector active area 26, as internal stray light. A specular ray 40 reflecting off of a 100 degree step 36 is directed away from the sample aperture 22, and is less likely to reach the detector active area 26 after reflecting off of the aperture 22. In modeling, the reflectance was measured off of a mirror sample to determine internal specular light rejection. The readhead with a 90 degree step 34 hitting mirror reflectance of 0.17% R, while the 100 degree step 36 had a mirror reflectance of 0.07% R. The 100 degree step 36 design provides an improvement in internal stray light rejection.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the claimed invention, which is set forth in the following claims.

What is claimed is:

1. An illumination source comprising:
   a first monochromatic illumination source comprising an associated illumination center-wavelength and associated illumination tolerance, wherein the source emits rays defining an illumination path; and
   a bandpass filter positioned in the illumination path, wherein the filter comprises an associated filter center-wavelength and an associated filter tolerance, and wherein
   the filter tolerance is no greater than approximately one-half the illumination tolerance and
   the filter center-wavelength is approximately within a range from about the illumination center-wavelength minus the illumination tolerance to about the illumination center-wavelength plus the illumination tolerance.

2. The illumination source of claim 1, wherein:
   the monochromatic illumination source is an LED;

the illumination center-wavelength is approximately 700 nm; and the illumination tolerance is no greater than about 20 nm.

3. The illumination source of claim 2, comprising:
a second illumination source emitting rays defining another illumination path reflecting off of the filter in a first direction, wherein the first illumination source and second illumination source are arranged relative to the filter such that rays from the first illumination source pass through the filter in the first direction, whereby the first and second illumination sources provide coaxial illumination.

4. The illumination source of claim 3, wherein the second illumination source is an LED comprising an associated center-wavelength of approximately 940 nm.

5. The illumination source of claim 3, wherein the illumination path associated with the second illumination source is positioned roughly 90 degrees relative to the illumination path associated with the first illumination source.

6. The illumination source of claim 1, comprising a second illumination source emitting rays defining another illumination path reflecting off of the filter in a first direction, wherein:
the first illumination source is an LED having an associated illumination center-wavelength approximately within a range from about 680 nm to about 960 nm;
the second illumination source is an LED comprising an associated illumination center-wavelength approximately within a range from about 510 nm to 740 nm; and
the first illumination source and the second illumination source are arranged relative to the filter such that rays from the first illumination source pass through the filter in the first direction.

7. The illumination source of claim 6, wherein:
the illumination center-wavelength associated with the first illumination source is approximately within a range from about 700 nm to about 740 nm; and
the illumination center-wavelength associated with the second illumination source is approximately within a range from about 510 nm to about 550 nm.

8. The illumination source of claim 7, wherein the illumination tolerance is not greater than about 20 nm.

9. A readhead comprising:
a first LED having a first center-wavelength associated therewith and being adapted to emit a first path of light;
a second LED having a second center-wavelength associated therewith and being adapted to emit a second path of light intersecting the first path of light at an intersection;
a beam splitter positioned at the intersection and having a bandpass filter associated therewith, wherein:
the first LED, the second LED and the beam splitter are arranged to provide coaxial illumination in a first direction,
the bandpass filter comprises a relatively narrow bandpass compared to a bandwidth associated with the first LED,
at least a portion of the coaxial illumination is reflected off a sample creating diffuse reflected light; and
the readhead further comprises a detector located to receive at least a portion of the diffuse reflected light.

10. The readhead of claim 9, wherein:
the bandwidth associated with the first LED is approximately 100 nm; and
the narrow bandpass is approximately 25 nm.

11. The readhead of claim 9, wherein the first and second LEDs have associated tolerances not greater than 20 nm and the bandpass filter has an associated tolerance of not greater than 10 nm.

12. The readhead of claim 9, comprising a light-scattering section upstream of the detector, wherein the light-scattering section comprises a plurality of steps formed at predefined angles greater than 90 degrees.

13. The readhead of claim 12, wherein the predefined angles at which the steps are formed are not less than approximately 100 degrees.

14. A readhead adapted for use in a monitoring system adapted to receive a sample on a sample aperture and determine a parameter value based on analyzing the sample, the readhead comprising:
a first LED having a first center-wavelength and a first tolerance associated therewith and being adapted to emit a first path of light;
a beam splitter comprising a bandpass filter positioned in the first path of light and having a filter center-wavelength and a filter tolerance associated therewith;
a second LED positioned relative to the first LED and the beam splitter and having a second center-wavelength and a second tolerance associated therewith and being adapted to emit a second path of light intersecting the beam splitter, wherein:
the second LED, the beam splitter and first LED are positioned to provide coaxial illumination of the sample by the first and second LEDs,
the filter tolerance is less than the first tolerance,
the bandpass filter comprises a relatively narrow bandpass compared to a bandwidth associated with the first LED; and the readhead further comprises:
a face defining an exit aperture through which the coaxial illumination passes, wherein the sample aperture is spaced a predetermined distance from the face and positioned to be illuminated by the coaxial illumination, such that when the sample is located on the sample aperture, the sample will reflect at least a portion of the coaxial illumination; and
a detector adapted to detect diffuse light resulting from the reflected illumination.

15. The readhead of claim 14, wherein the filter tolerance is less than the second tolerance.

16. The readhead of claim 14, wherein the bandwidth of the first LED is approximately 100 nm and the filter bandpass is approximately 25 nm.

17. The readhead of claim 14, wherein at least light from the first LED is filtered by the filter.

18. The readhead of claim 15, wherein light from the second LED is reflected off the filter to provide the coaxial illumination with light from the first LED passing through the filter.

19. The readhead of claim 14, wherein the second center wavelength is higher than the filter center-wavelength and the first center-wavelength.

20. The readhead of claim 19, wherein the filter tolerance is less than the second tolerance.

21. The readhead of claim 20, wherein the filter tolerance is not greater than about 10 nm.

22. The readhead of claim 21, wherein the first center-wavelength is about 700 nm and the second center-wavelength is about 940 nm.

23. The readhead of claim 14, comprising a light-scattering section associated with the detector, wherein the light-scattering section comprises a plurality of steps defining one or more angles greater than 90 degrees and positioned to reduce internal stray light reaching an active area of the detector.

24. A readhead adapted for use in a monitoring system adapted to receive a sample on a sample aperture and determine a parameter valve based on analyzing the sample, the readhead comprising:

a first LED having a first center-wavelength associated therewith and being adapted to emit a first path of light, the first LED having associated therewith a first bandwidth and a first tolerance;

a beam splitter positioned in the first path of light, the beam splitter comprising a filter;

a second LED positioned relative to the first LED and the beam splitter and having a second center-wavelength associated therewith and being adapted to emit a second path of light intersecting the beam splitter, the second LED having associated therewith a second bandwidth and a second tolerance, the second center-wavelength being greater than the first center-wavelength, wherein the filter has associated therewith a filter bandpass being relatively narrow compared to the first bandwidth and the second bandwidth, the first and second paths of light interact with the beam splitter forming a beam of illumination comprising light from the first LED and the second LED; and the readhead further comprises a face defining an exit aperture through which the beam passes, wherein the sample aperture is spaced from the face and positioned to be illuminated by the beam such that when the sample is located on the sample aperture, the sample will reflect at least a portion of the beam;

a detector comprising an active area and a detection aperture positioned to receive at least a portion of diffuse light resulting from the reflected beam; and a light-scattering section positioned upstream of the detector active area, wherein the light-scattering section comprises a plurality of steps defining one or more angles greater than 90 degrees and the section is positioned such that the steps are angled to reduce stray internal light on the detector active area.

25. The readhead of claim 24, wherein the one or more angles defined by the plurality of steps are approximately 100 degrees.

26. The readhead of claim 25, wherein:

the bandpass filter has a filter center-wavelength and a filter tolerance associated therewith; and the filter center-wavelength and filter tolerance are selected to separate wavelengths associated with the first LED from wavelengths associated with second LED such that the light in the beam from the first LED does not have wavelengths equal to wavelengths of light in the beam from the second LED.

27. The readhead of claim 25, wherein the filter has associated therewith a filter center-wavelength less than approximately the second center-wavelength plus the second tolerance.

28. The readhead of claim 27, wherein the filter center-wavelength is less than approximately the first center-wavelength plus the first tolerance.

29. The readhead of claim 28, wherein the filter center-wavelength is less than approximately the first center-wavelength minus the first tolerance.

30. The readhead of claim 28, wherein the filter center-wavelength is less than approximately the first center-wavelength minus 20 nm.

31. The readhead of claim 30, wherein the filter has associated therewith a tolerance less than approximately 20 nm.

* * * * *